(12) United States Patent
Goyal et al.

(10) Patent No.: US 7,297,110 B2
(45) Date of Patent: Nov. 20, 2007

(54) SYSTEMS AND METHODS FOR REMOTE MONITORING OF FEAR AND DISTRESS RESPONSES

(76) Inventors: Muna C. Goyal, P.O. Box 2087, Tarpon Springs, FL (US) 34688; Rajiva Goyal, P.O. Box 2087, Tarpon Springs, FL (US) 34688

( * ) Notice: Subject to any disclaimer, the term of this patent is extended or adjusted under 35 U.S.C. 154(b) by 0 days.

(21) Appl. No.: 11/007,391

(22) Filed: Dec. 8, 2004

(65) Prior Publication Data

US 2006/0047187 A1   Mar. 2, 2006

Related U.S. Application Data

(60) Provisional application No. 60/605,239, filed on Aug. 27, 2004.

(51) Int. Cl.
*A61B 5/00* (2006.01)
(52) U.S. Cl. .................................. 600/300; 128/920
(58) Field of Classification Search ........ 600/300–301; 128/903–905, 920–921; 340/573.1
See application file for complete search history.

(56) References Cited

U.S. PATENT DOCUMENTS

| | | | |
|---|---|---|---|
| 5,629,578 A | 5/1997 | Gargano et al. | |
| 6,013,007 A | 1/2000 | Root et al. | |
| 6,443,890 B1 * | 9/2002 | Schulze et al. | 600/300 |
| 6,463,385 B1 | 10/2002 | Fry | |
| 6,478,736 B1 * | 11/2002 | Mault | 600/300 |
| 6,513,532 B2 * | 2/2003 | Mault et al. | 128/921 |
| 6,579,231 B1 * | 6/2003 | Phipps | 600/300 |
| 6,741,935 B1 | 5/2004 | Eschenbach | |

OTHER PUBLICATIONS http://www.prnewswire.co.uk/cgi/news/release?id=122097.
http://www.virtualtechnologiesltd.com/Virtual_Shadow/VirtualTrack.htm.
http://www.npwrc.usgs.gov/resource/2002/radiotrk/radiotrk.pdf.
http://www.frwd.com.
http://www.digitalangel.net/consumer.asp.
https://www.gpsanywhere.com.
http://www.gpschildlocatorwatch.com.
http://www.revelationwebsite.co.uk/index2/rev/digi.htm.

* cited by examiner

*Primary Examiner*—Max F. Hindenburg
*Assistant Examiner*—Michael C Astorino
(74) *Attorney, Agent, or Firm*—Casimic Jones, S.C.

(57) ABSTRACT

The present invention relates to systems and methods for tracking and monitoring the location, health, emotional state, position, environment, sound, appearance, and other characteristics of subjects remotely over an electronic communications network by receiving signals transmitting such information from a device or devices located on or in the subject to a remote monitoring device over the electronic communications network.

20 Claims, 6 Drawing Sheets

SYSTEMS AND METHODS FOR REMOTE MONITORING OF FEAR AND DISTRESS RESPONSES

The present invention claims priority to U.S. Provisional Patent Application Ser. No. 60/605,239, filed Aug. 27, 2004, herein incorporated by reference in its entirety.

FIELD OF THE INVENTION

The present invention relates to systems and methods for tracking and monitoring the location, health, emotional state, position, environment, sound, appearance, and other characteristics of subjects remotely over an electronic communications network by receiving signals transmitting such information from a device or devices located on or in the subject to a remote monitoring device over the electronic communications network.

BACKGROUND

Many undesired events occur that can adversely impact an individual's health, well-being, and/or safety. Such events include accidents, unexpected adverse health events (e.g., heart problems, seizures, heat stroke, dizziness, breathing problems, bleeding, broken bones, burns, chemical exposure, etc.), abductions, criminal acts, and the like. Many of such events, if known to others in a position to assist the individual (e.g., physicians, emergency response workers, law enforcement, family, friends, caretakers, etc.), can be avoided or their negative effects minimized or ameliorated. Unfortunately, many such events occur in a manner in which assistance is unavailable or arrives too late. What is needed are improved systems and methods for avoiding or reducing the impact of such adverse events.

SUMMARY OF THE INVENTION

The present invention relates to systems and methods for tracking and monitoring the location, health, emotional state, position, environment, sound, appearance, and other characteristics of subjects remotely over an electronic communications network by receiving signals transmitting such information from a device or devices located on or in the subject to a remote monitoring device over the electronic communications network.

For example, in some embodiments, the present invention provides a system for remote monitoring of a subject, where the system comprises a processor or software configured to carry out one or more of the following functions: a) receive a transmitted signal from a remote device on or in a subject; b) convert the transmitted signal into a format that permits display of data corresponding to the transmitted signal on a display device; c) organize the data so as to display a characteristic of the subject on the display device; and d) provide secured access to the display of the characteristic to a user registered to access information related to the subject.

The present invention is not limited by the nature of the subject that is monitored. In preferred embodiments, the subject is a human or a group of humans (e.g., a child, a medical patient, an athlete or athletic team, a criminal or other person monitored for security reasons, an elderly individual, etc.). In some embodiments, the subject is a non-human animal (e.g., a domestic pet, livestock, a research animal, a wild animal, an endangered or protect species, etc.).

The present invention is not limited by the nature or location of the processor or software. In some embodiments, the processor is located in a computer. In some embodiments, the processor is located in a hand-held device (e.g., phone, watch, personal digital assistant, etc.).

The present invention may be utilized with any type of signal source sent from the remote device, including, but not limited to satellite, cable, telephone, radio, low frequency signals, etc.

The present invention is also not limited by the nature of the remote device. In some embodiments, the remote device comprises a microchip embedded in a subject. In some embodiments, the remote device is a small electronic device carried by or attached to the subject (e.g., a phone, watch, arm or leg band, personal digital assistant, etc.). In some embodiments, the remote device comprises a video input device, a microphone, electrodes, analyte detection sensors (e.g., for detecting chemical components of skin, tissue, or body fluids), etc. In some embodiments, the remote device comprises a means for administering a medical intervention to the subject. In some embodiments, the remote device comprises a means for administering a drug (e.g., tranquilizer). In some embodiments, the remote device comprises a means for obtaining the attention of the subject, including, for example, through use of an alarm, heat, electrical shock, and the like. In some embodiments, the remote device comprises a means for contacting emergency personnel in the vicinity of the subject. For example, in some embodiments, the location of the subject is transmitted from the remote device to the processor, the processor identifies the emergency response personnel nearest to the subject (e.g., by searching the Internet, a database, etc.), and provides contact information for the emergency response personnel to the remote device.

The present invention is not limited by the nature of the method or system by which information is displayed to a user. In some embodiments, the display device comprises a computer or television monitor. In some embodiments, the display device comprises a handheld electronic device.

In some preferred embodiments, the processor is configured to receive and display information over an Internet or other public or private communication network so that the user can access the information from any desired location or device.

The present invention may be used to monitor any one or more characteristics of the subject obtained from the remote device and transmitted to the system. In preferred embodiments, the characteristic is a physiological response, including, but not limited to, a fear response (e.g., fear, duress, etc.), drowsiness/sleep, sexual arousal, etc. of the subject. In other embodiments, the characteristic is a medical or health characteristic (e.g., heart rate, body temperature, breathing rate or quality, blood sugar, hormone level, compounds or conditions corresponding to an immune or allergic response, the presence of or change in condition of a lesion, neurological function, etc.). In other embodiments, the characteristic relates to the location or position of the subject or to the environment of the subject. In some embodiments, the characteristic relates to the appearance or sound of the subject.

In some embodiments, the system is configured to monitor the characteristic of the subject at two or more time points or continuously. In some such embodiments, the time points are selected by the user. In some embodiments, the time points occur at regular intervals (e.g., every minute, every 15 minutes, every hour, etc.). In some embodiments, the monitoring is passive, but where a change in or nature of the detected characteristic(s) fall outside of a desirable range (e.g., safe range, healthy range, permissible range), the user is alerted.

The systems of the present invention are not limited by the distance between the remote device/subject and the processor/user. For example, the distance may be at least 100 yards, . . . a mile . . . , 10 miles . . . , 100 miles, . . . etc.

In some preferred embodiments, the processor stores information about the user and/or subject (e.g., for security management, medical monitoring, etc.).

The present invention also provides methods for monitoring a subject remotely. For example, in some embodiments, the methods of the present invention comprise one or more of the following steps:
 a) accessing an electronic monitoring device;
 b) verifying user identification on the electronic monitoring device;
 c) selecting a monitoring option for monitoring a characteristic of a geographically remote subject having a remote device that transmits a signal carrying information about the characteristic; and
 d) viewing information about the characteristic on the electronic monitoring device.

The method may be employed using any of the features of the systems of the invention described above.

The present invention further comprises kits or containers containing components useful for practicing such methods. For example, the present invention provides kits or containers comprising: a) software configured to carry any of the above mentioned methods; and b) a remote device.

DEFINITIONS

Figure 1:
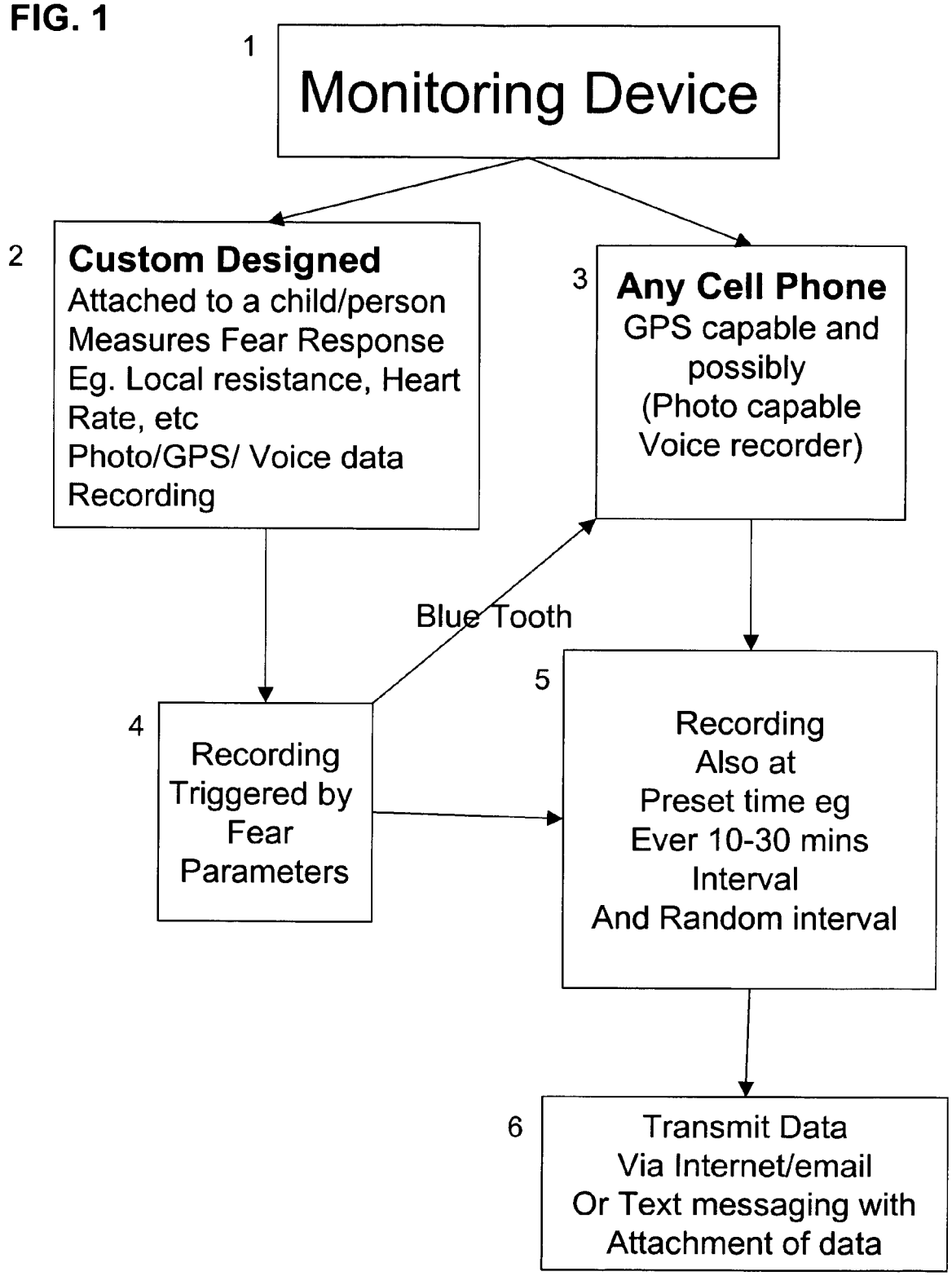
FIG. 1 shows monitoring device uses in some embodiments of the present invention.

To facilitate an understanding of the present invention, a number of terms and phrases are defined below:

As used herein, the terms "computer memory" and "computer memory device" refer to any storage media readable by a computer processor. Examples of computer memory include, but are not limited to, random access memory (RAM), read-only memory (ROM), computer chips, optical discs (e.g., compact discs (CDs), digital video discs (DVDs), etc.), magnetic disks (e.g., hard disk drives (HDDs), floppy disks, ZIP® disks, etc.), magnetic tape, and solid state storage devices (e.g., memory cards, "flash" media, etc.).

As used herein, the term "computer readable medium" refers to any device or system for storing and providing information (e.g., data and instructions) to a computer processor. Examples of computer readable media include, but are not limited to, optical discs, magnetic disks, magnetic tape, solid-state media, and servers for streaming media over networks.

As used herein, the terms "processor" and "central processing unit" or "CPU" are used interchangeably and refer to a device that is able to read a program from a computer memory device (e.g., ROM or other computer memory) and perform a set of steps according to the program.

As used herein, the term "encode" refers to the process of converting one type of information or signal into a different type of information or signal to, for example, facilitate the transmission and/or interpretability of the information or signal. For example, audio sound waves can be converted into (i.e., encoded into) electrical or digital information. Likewise, light patterns can be converted into electrical or digital information that provides an encoded video capture of the light patterns.

As used herein, the term "client-server" refers to a model of interaction in a distributed system in which a program at one site sends a request to a program at another site and waits for a response. The requesting program is called the "client," and the program that responds to the request is called the "server." In the context of the World Wide Web, the client is a "Web browser" (or simply "browser") that runs on a computer of a user; the program which responds to browser requests by serving Web pages is commonly referred to as a "Web server."

As used herein, the term "Internet" refers to any collection of networks using standard protocols. For example, the term includes a collection of interconnected (public and/or private) networks that are linked together by a set of standard protocols (such as TCP/IP, HTTP, and FTP) to form a global, distributed network. While this term is intended to refer to what is now commonly known as the Internet, it is also intended to encompass variations that may be made in the future, including changes and additions to existing standard protocols or integration with other media (e.g., television, radio, etc). The term is also intended to encompass non-public networks such as private (e.g., corporate) Intranets.

As used herein, the term "security protocol" refers to an electronic security system (e.g., hardware and/or software) to limit access to the processor to specific users authorized to access the processor. For example, a security protocol may comprise a software program that locks out one or more functions of a processor until an appropriate password is entered.

As used herein, the term "resource manager" refers to a system that optimizes the performance of a processor or another system. For example, a resource manager may be configured to monitor the performance of a processor or software application and manage data and processor allocation, perform component failure recoveries, optimize the receipt and transmission of data, and the like. In some embodiments, the resource manager comprises a software program provided on a computer system of the present invention.

As used herein, the term "in electronic communication" refers to electrical devices (e.g., computers, processors, communications equipment, etc.) that are configured to communicate with one another through direct or indirect signaling. For example, a computer configured to transmit (e.g., through cables, wires, infrared signals, telephone lines, satellite, etc) information to another computer or device, is in electronic communication with the other computer or device.

As used herein, the term "transmitting" refers to the movement of information (e.g., data) from one location to another (e.g., from one device to another) using any suitable means.

As used herein, the term "subject" refers to any animal (e.g., a mammal), including, but not limited to, humans, non-human primates, domestic pets, livestock, wild animals, aquatic animals, and the like.

DETAILED DESCRIPTION OF THE INVENTION

The present invention provides systems and methods for remote monitoring of subjects for a variety of purposes including, but not limited to, monitoring of children, patients, elderly, criminals, animals, and the like for safety, security, health, census, marketing, or any other desired purposes. Particularly preferred features of the present invention include the ability to monitor physiological responses such as fear from remote locations and to associate such responses with the identity of a subject and geographic location of a subject. Other particularly preferred features of the invention include the ability of a user to monitor the subject to access information remotely about the subject via a user-friendly system, preferably over an Internet connection via a secured service.

For example, a preferred use of the present invention is for parents to monitor children. In some such embodiments, the child has a remote device (e.g., on a wrist band) that monitors, for example, physiological or health characteristics of the child, as well as the geographic position of the child (e.g., via a global positioning system (GPS) or any other desired system). The remote device transmits a signal that is directly or indirectly accessible from a remote location by a parent. In some embodiments, Bluetooth technology (or other wireless local area networking techniques, such as High Performance Radio Local Area Network (HiperLAN) or Broadband Radio Access Network (BRAN)) is used to transmit a signal from the device that measures physiological information to a cell phone. Preferably, the parent is provided with software that permits secure access to an Internet service that allows the parent, from any desired location, to access characteristics of his or her child that are recorded and transmitted by the remote device. In some preferred embodiments, the parent accesses the information from a small hand-held device, such as a mobile phone. In some embodiments, the parent accesses the information at any desired time. In other embodiments, a system continuously monitors the child and alerts the parent (e.g., via alarm, phone call, etc.) when a characteristic is measured that is outside of a predetermined threshold or range, indicating trouble or potential trouble for the child. For example, the remote device measures physiological parameters that permit detection of a fear response. When threshold values are reached that correlate to a fear response, the parent is alerted and informed about the fear response and the location of the child. The parent may then take the appropriate actions. In some embodiments, the remote device transmits audio or video information that assists the parent in evaluating the child's safety. The systems of the present invention allow the parent the flexibility to set a variety of desired parameters associated with such monitoring.

In another example, a healthcare worker (e.g., physician, nurse, sport trainer, etc.) monitors subjects (e.g., patients, athletes, etc.) from a remote location to assess a subject's or group of subjects' health, or to be alerted if the health of the subject or subjects is compromised. In some preferred embodiments, the remote device or an associated device provides a means through which the healthcare worker can remotely provide a medical intervention to assist the subject or subjects.

Certain non-limiting illustrative embodiments of the systems and methods of the present invention are highlighted below. One skilled in the art will appreciate a variety of variations on these systems and methods (and those described above) that are within the scope of the invention, as well as a wide variety of applications of the invention.

A variety of monitoring technologies exist and may be incorporated into the systems and methods of the present invention. Such technologies include, but are not limited to, those described in U.S. Pat. Nos. 5,629,678 to Gargano et al., and 6,741,935 to Eschenbach (both of which are hereby incorporated by reference in their entireties). Commercially available monitoring technologies include products sold under the brand names Benefon Seraph NT, Digital Angel, ETerraFind, eWorldTrack, Followit, FRWD, GPS Child Locator, G-Trac Locator, G-Trac Phone, Kidbug, KidContact, Leonie, POMALS ActivePak, PowerLOC, Satsafe, SECUPOD, TRACER, TRAXER, uLocate, Virtual Track, WalkMate, and Wherify.

FIG. 1 shows information flow from a remote device (monitoring device (1)) in some embodiments of the present invention. In some embodiments, the monitoring device is custom designed (2) and can be attached to a subject and measure any desired characteristic. In other embodiments, the monitoring device is adapted from a preexisting device such as a mobile telephone (3) and is configured to detect the desired characteristic of the subject. In some embodiments, the recording of the characteristic is triggered by the emergence or appearance of the characteristic (4) (e.g., recording is triggered upon a fear response). In some embodiments, recording occurs at preset time intervals or at random intervals (5). The recorded information (data) is transmitted via any desired means either directly or as an attachment of a notification message (6) (Internet, e-mail, text messaging, etc.).

Figure 2:
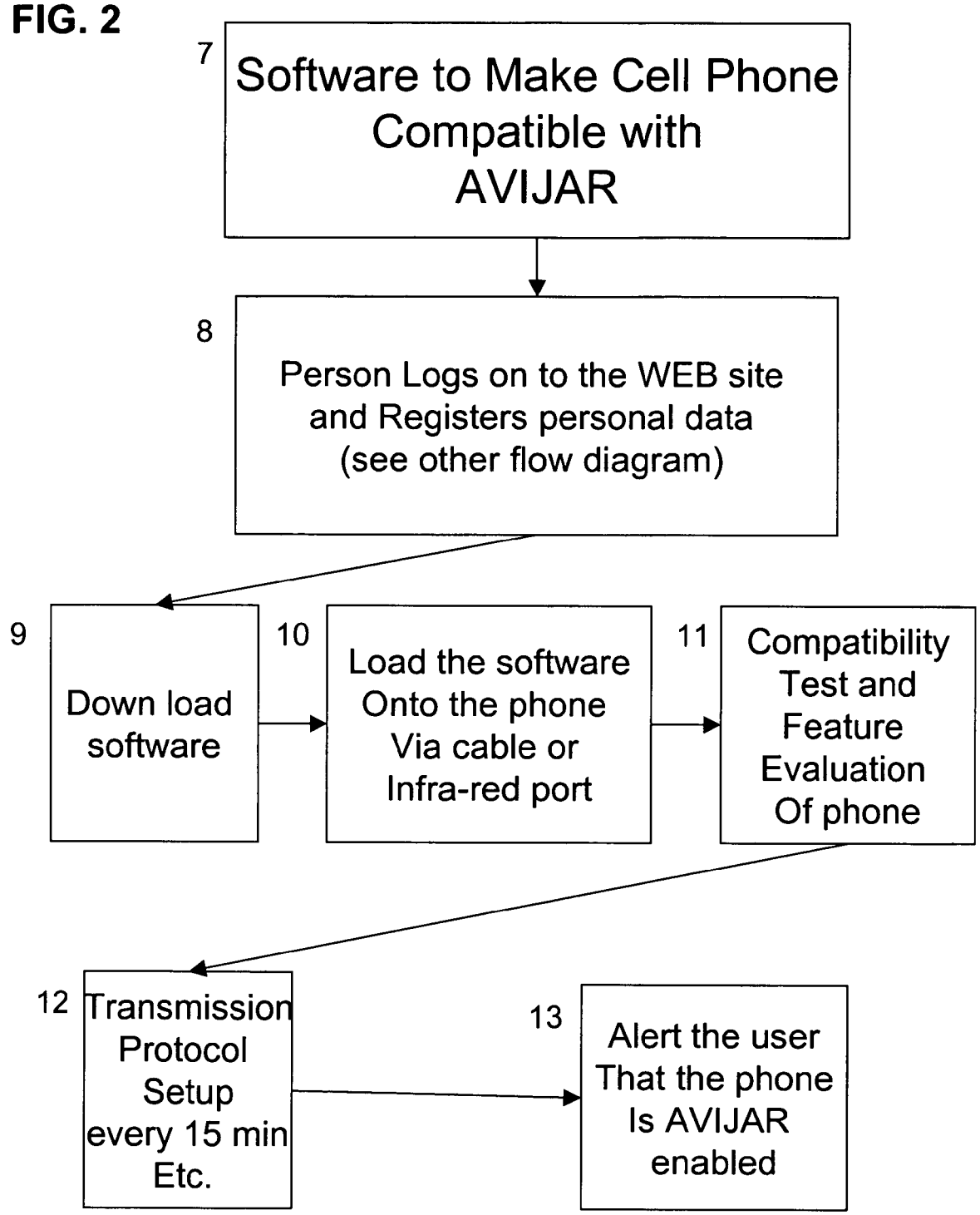
FIG. 2 shows software uses in some embodiments of the present invention.

FIG. 2 shows a software configuration (7) in some embodiments of the present invention. In some embodiments, a user uses a client application (e.g., a Web browser) to access a remote server application (e.g., a Web server), and creates or accesses a preexisting secure account (8). The user may then download software (9) from the server to enable remote monitoring functionality in a hand-held device such as a mobile telephone. After downloading, the software is transmitted from the client device to the mobile telephone by any suitable means (10) (e.g., via a data cable or an infrared port). The user may then use the software transferred to the mobile telephone to perform a compatibility test with the remote monitoring system, and/or an evaluation of the remote monitoring features available via the mobile telephone (11). After the user has verified compatibility with the remote monitoring system, and has become familiar with the remote monitoring features of the mobile telephone, the user may configure the desired parameters for remote monitoring (12) (e.g., data transmission protocols, time intervals between transmissions, etc.). For example, the software may be configured to transmit or receive data every 15 minutes. After the software has been configured, the remote monitoring system alerts the user (e.g., via the mobile telephone itself, a Web browser, an e-mail or text message, etc.) that remote monitoring functionality has been enabled for the mobile telephone (13).

Figure 3:
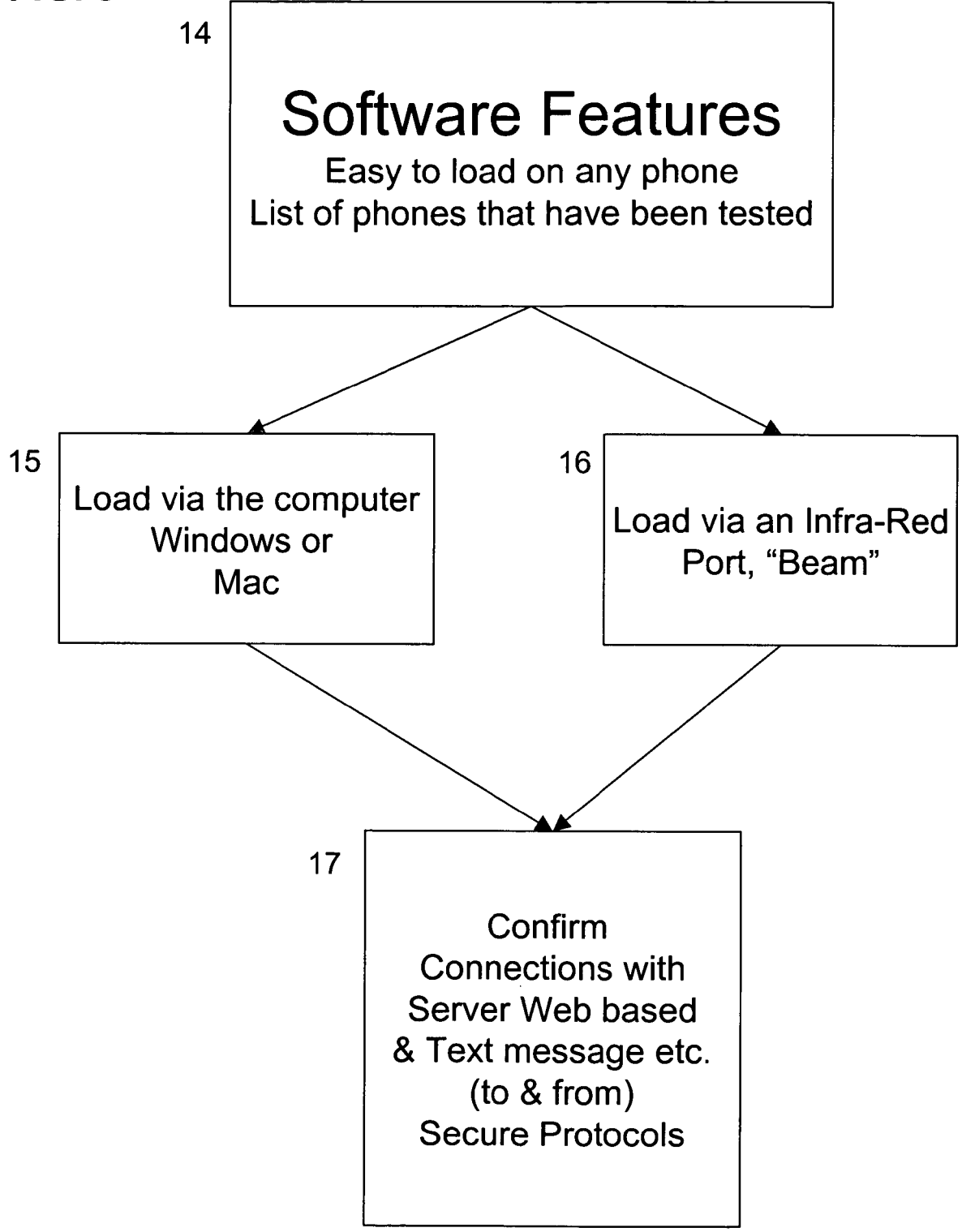
FIG. 3 shows software features in some embodiments of the present invention.

FIG. 3 shows a software configuration to enable remote monitoring functionality in a mobile telephone (14) in some embodiments of the present invention. In some embodiments, a user uses a computer-based client application (e.g., a Web browser) to access a remote server application (e.g., a Web server), and downloads software from the server to enable remote monitoring functionality in a mobile telephone. The remote monitoring system may be accessed by a client computer using any suitable operating system (e.g., Windows, Mac OS, UNIX, Linux, etc.). The software may then be transferred from the computer to the mobile telephone via a physical connection (15) (e.g., a data cable). Alternatively, the software may be transferred to the mobile telephone via a wireless connection (e.g., infrared port, bluetooth, wireless network, etc.) from either a suitably equipped computer or any transmitting device (16) (e.g., another mobile telephone, a hand-held computing device or personal digital assistant (PDA), a terristrial antenna, a satellite, etc.). Once the software has been transferred to the mobile telephone, the user may verify compatibility with the remote monitoring system, and configure the desired parameters for remote monitoring (17) (e.g., data transmission protocols, time intervals between transmissions, etc.).

Figure 4:
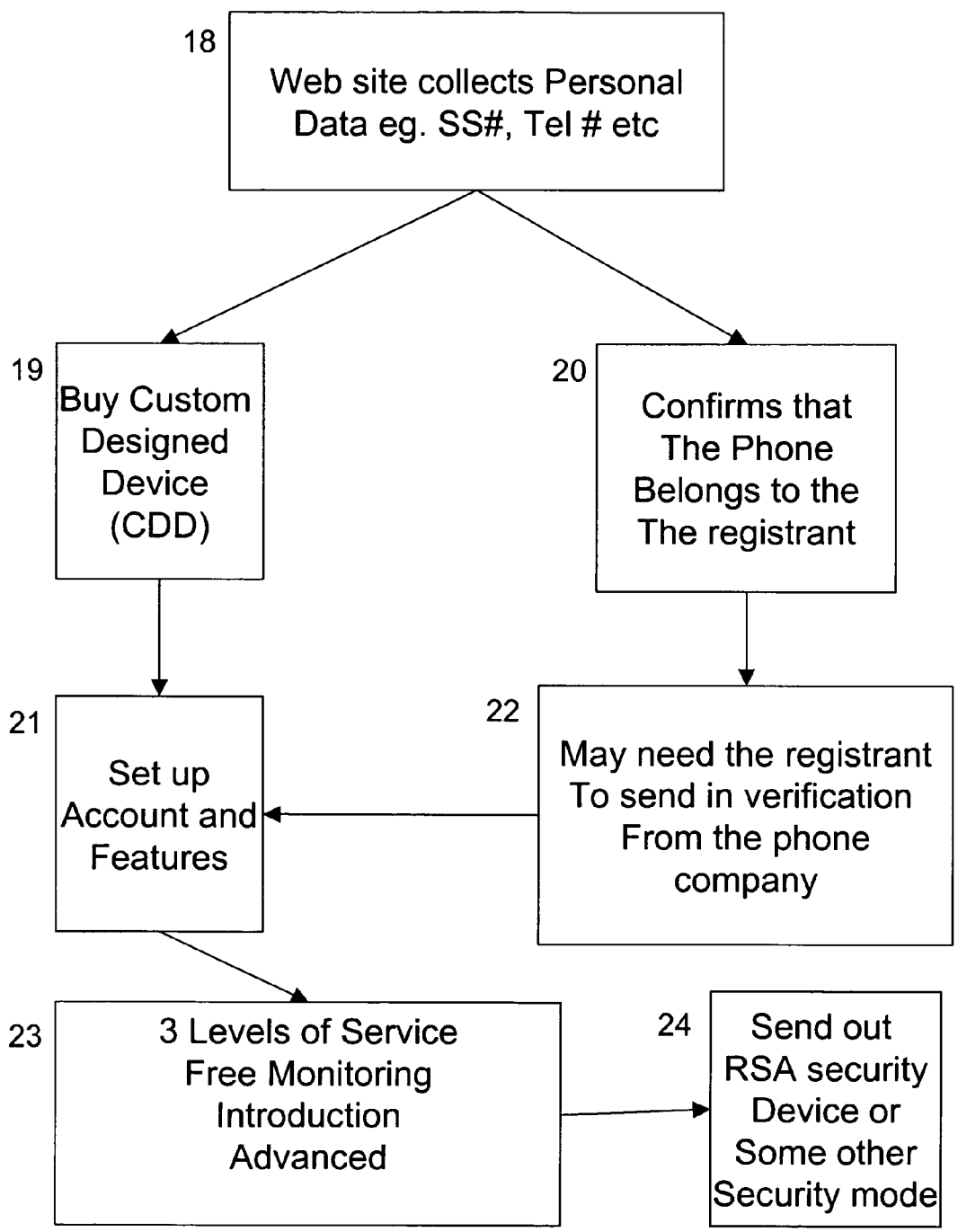
FIG. 4 shows Internet features in some embodiments of the present invention.

FIG. 4 shows a software configuration to enable remote monitoring capability over a computer network such as the Internet. In some embodiments, a user uses a computer-based client application (e.g., a Web browser) to access a remote server application (e.g., a Web server) for the purpose of establishing an account with a remote monitoring service. Upon accessing the remote server (e.g., the Web site associated with the remote monitoring service), the user may input identifying information (e.g., name, Social Security number, contact and billing information, etc.) and data necessary to create a secure account with the remote monitoring service (18). If the user does not have a suitable remote monitoring device, the remote monitoring service may offer stock or custom-designed remote monitoring devices (e.g., mobile telephones, hand-held computers, etc.) for purchase via the Web site (19). If the user already has a suitable remote monitoring device (e.g., an appropriately configured mobile telephone), the user may then input verifying information via the Web site to allow the remote monitoring service to confirm the user's identity and ownership of the remote monitoring device (20). For additional security, the remote monitoring service may require the user to provide independent verification from a third party (22) (e.g., the user's mobile telephone service provider). After the user has registered the remote monitoring device, the user may then use the Web site to configure the desired parameters of the account, access the features of the account, and select a desired level of remote monitoring service (21). For example, the account may offer multiple levels of service (23) (e.g., free basic monitoring, introductory monitoring, advanced monitoring, etc.). Once the account is fully configured, the Web site can provide secure access to the remote monitoring service using security measures (24) (e.g., RSA encryption). The present invention is not limited by the nature of the security measure taken. In some embodiments, a questions is asked that requires a specific response known only to the authorized users (e.g., child's name, pet name, mother's maiden name, etc.).

Figure 5:
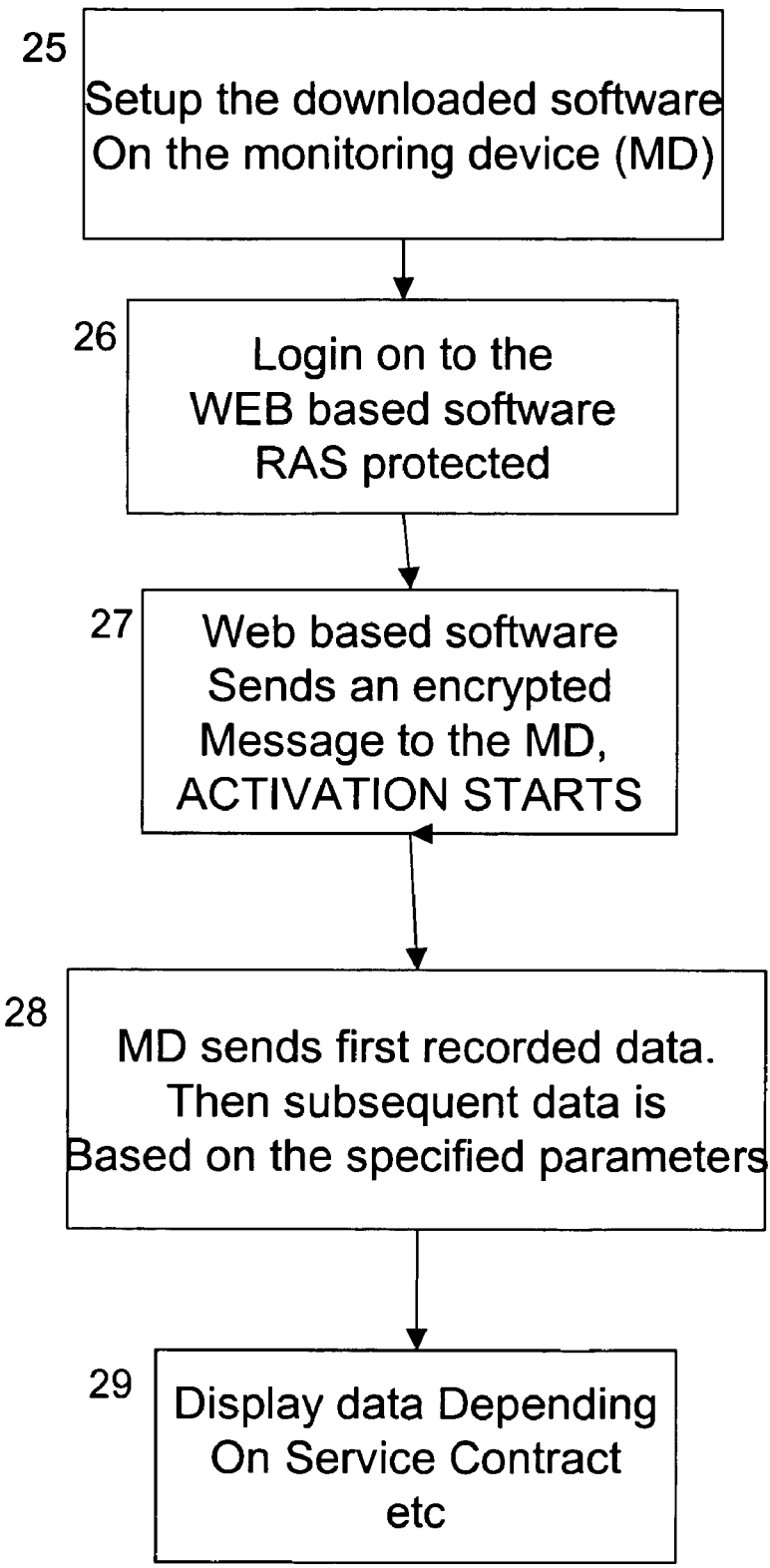
FIG. 5 shows Internet features in some embodiments of the present invention.

FIG. 5 shows a software configuration to enable remote monitoring capability in a remote monitoring device using a computer network such as the Internet. In some embodiments, a user accesses software that has been transferred from a transmitting device to a remote monitoring device, and configures the software in the remote monitoring device to allow it to communicate with a remote server (25). The user may then access a secure account with the remote monitoring service via a client application such as a Web browser (26). The user may activate the remote monitoring functionality of the remote monitoring device by instructing the remote server, via a Web browser, to send an encrypted activation signal to the remote monitoring device (27). Upon activation, the remote monitoring device records and transmits initial information related to the characteristics to be monitored (28). Subsequent data transmissions from the remote monitoring device may occur at user-defined time intervals that are configured via the Web site (28). The Web site can then display the data transmitted from the remote monitoring device, according to the level of service selected and other user-defined monitoring parameters (29).

Figure 6:
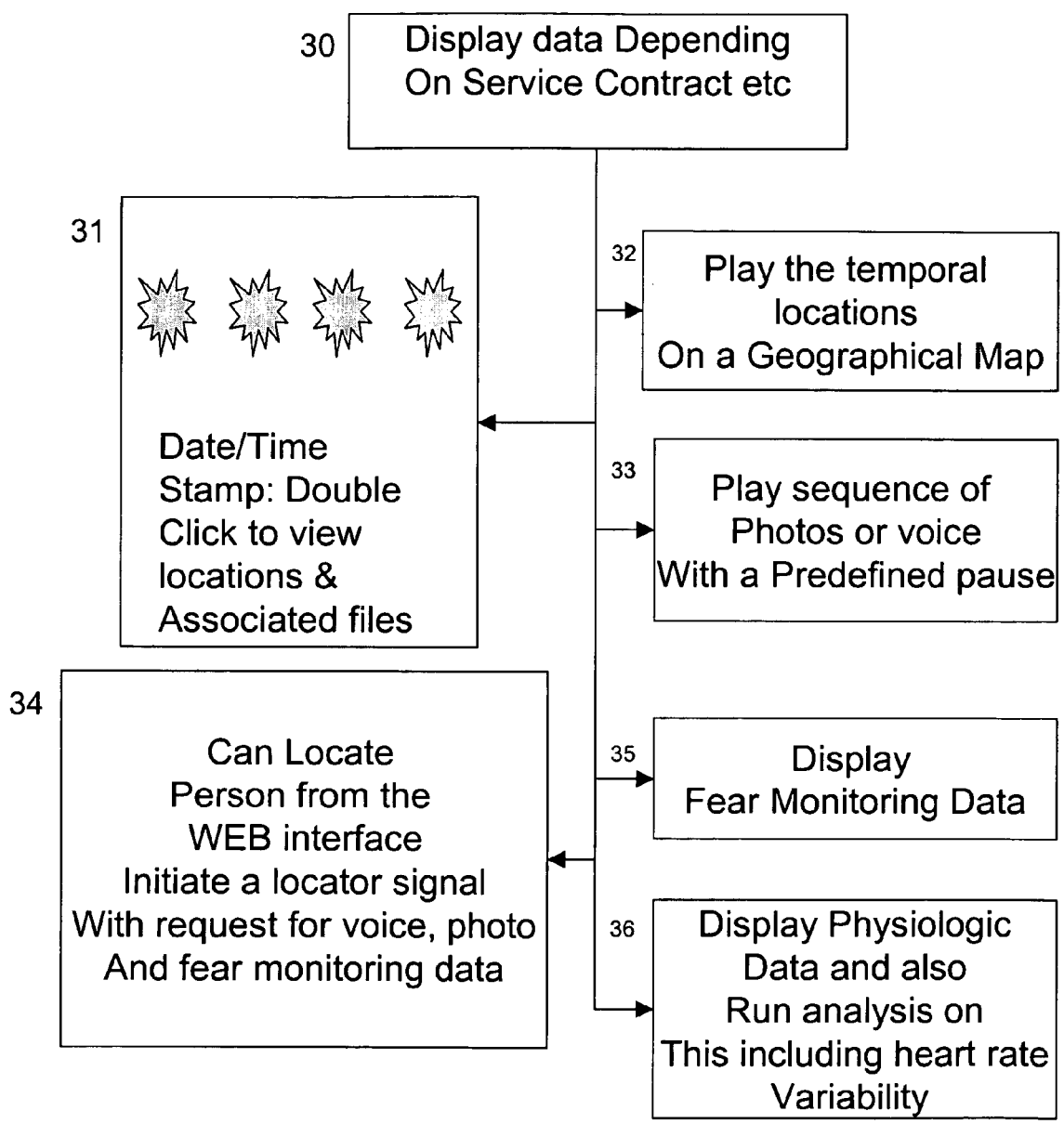
FIG. 6 shows Internet features in some embodiments of the present invention.

FIG. 6 shows a software configuration to enable remote monitoring capability over a computer network such as the Internet. In some embodiments, a user uses a computer-based client application (e.g., a Web browser) to access a secure account with the remote monitoring service (e.g., via the service's Web site). The Web site can display data transmitted from a remote monitoring device, according to the level of service selected and other user-defined monitoring parameters (30). The Web site software can display numerous monitored characteristics, either separately or simultaneously. For example, the software can assign a date/time stamp to each event recorded and transmitted by the remote monitoring device, and allow a user to view and sort the recorded data according to date or time (31). In addition, the software can display information about the geographic location of the subject being monitored, either at preset time intervals or upon a user-initiated location request (34). A user-initiated location request can also include other monitored characteristics, such as voice data, photographic data (e.g., a picture of the subject or the subject's ambient environment), or other data such as fear monitoring data (34). The Web-based software may include additional features, such as the ability to display a subject's temporal locations on a geographic map (32); the ability to play a sequence of photographs or voice data items, with or without preset, user-defined, or random pauses (33); the ability to display fear monitoring data for a subject (35); and the ability to display and analyze a subject's physiological characteristics (36) (e.g., heart rate, vital signs, etc.). The technology may be used for any number of additional applications. For example, a group of friends, family, colleagues, etc. can set up a network and the location of the individuals can be mapped on a portable device, etc. The group can look up the locations of the other members and the system can give recommendations as to the restaurants, nightclubs, meeting places, etc. In some embodiments, a company can sign up with the system to track employees and be able to allocate resources depending on need. For example, installation companies or repair companies can get the closest technician to an emergency.

EXAMPLE 1

Fear Response Monitoring

This example describes an illustrative fear response monitoring system for parents to use with children. The child has a wrist band affixed to a series of sensors, a GPS, a smart processor trigger "alarms" when a fear response is detected, and a wireless signaling device such that a parent can monitor the health and well being of the child remotely. The wristband is configured to detect stress such than an alarm or alert condition is triggered for parental immediate attention. The sensor on the wristband comprises a galvanic skin resistance (GSR) sensor. GSR increases dramatically in the presence of sudden fright.

In some embodiments, the wristband is included in a glove, where the glove further comprises electrode attachments that contact the hands or fingers to give enhanced GSR response. Preferably, the electrodes are configured to minimize motion artifacts.

In some embodiments, the device further detects heart rate and/or oximetry to assess a fear response.

In some embodiments, the device further has a manual trigger that the child can activate, independent of the automatic fear response sensors.

In some embodiments, Bluetooth technology or other wireless local area networking techniques (e.g., High Performance Radio Local Area Network (HiperLAN) or Broadband Radio Access Network (BRAN)) are used to transmit the signal from the wristband to a cell phone. The information is then sent to the Internet.

When a fear response is detected, the device transmits a signal to the parent (e.g., a phone call, an Internet alarm, etc.). The transmission indicates when the fear response occurred and the location of the geographic child.

EXAMPLE 2

Fear Response System

In some embodiments, the present invention provides a fear response system that measures one or more physiological characteristics of a subject to assess fear/duress and provides remote monitoring of the fear response as well as geographic location of the subject and sound (e.g., voice) or video (e.g., photographic image) information about the subject. In some embodiments, the physiological characteristic is measured by one or more of galvanic skin resistance (GSR), heart rate, electrocardiogram (ECG), oximetry, and electroencephalogram (EEG).

In some embodiments, the system provides a skin covering (e.g., clothing, vest, wristband, etc.) containing a plurality of electrodes for measuring GSR. For example, in some preferred embodiments, electrodes are provides on a vest-type covering such that electrodes are positioned to contact each arm of a subject. GSR measurement is subject to substantial electrode motion artifact. Thus, proper electrode coupling and/or computational methods are used to minimize the artifact and permit clear indication of a larger emotional stress change compared to the smaller artifact.

GSR can increase due to certain emotional triggers that are not directly related to fear or duress (e.g., dislike, memory of prior pain, etc.). Thus, in preferred embodiments, the systems of the present invention provide secondary indicators of the status of the subject, such as audio or video monitoring. Such systems find particular use with parents monitoring children where, for example, the parent is willing to tolerate many false positive initial fear indications to ensure the safety of their child. This is particularly true where confirmation of the subject's safety is readily monitored. For example, in some embodiments, the parent received an alarm of a potential fear response and initiates a procedure to confirm the safety of the child. The confirmation may be audio or video monitoring, a call to the child, or a simple prompt that requires the child to push a button or other indicator, confirming their safety. There are a wide variety of other applications where secondary confirmations find use to discriminate false positive signals from real signals. For example, security personal monitoring prisoners or livestock can be prompted by an alarm to simply scan video information of the subject to determine whether a problem exists.

Experiments conducted during the development of the present invention sought to determine parameters of the system that provide the desired results. A wrist band device was assembled with steel electrodes and compared to a device having electrodes in contact with the hand. Measurements were made on several person and various threats and pain methods were used to elicit a GSR emotional response that affected two simultaneous GSR readings. The hand-electrode GSR gave 10% to 40% fluctuations of the GSR around a nominal 10K value whereas the wrist electrodes gave 2% to 6% fluctuations around a 60K nominal GSR. Thus, these experiments demonstrated that GSR variations from the wrist or hand could be used, although reduction in body motion artifact is important.

Experiments conducted during the development of the present invention developed novel means to compute electrode coupling impedance dynamically to substantially diminish motion artifact on the GSR measurement. The electrode to human interface was modeled as three series resistances with parallel capacitances. It is contemplated that the electrode to body capacitance is substantially larger than the body's equivalent parallel capacitance. Thus, by use of frequency sweeping or FFT analysis of the electrode to electrode impedance from, for example, 10 Hz to 30 Hz, then it is possible to compute or separate out the individual resistive components and then subtract the electrode resistance's dynamic changes.

Tests were conducted with different-sized electrodes. Results indicated that, unless skin preparation was used, the larger the area of the electrode, the better the result. Thus, for wrist-band type applications, a full wrist band sized electrode was better than coin sized electrodes. In particular, two stainless steel wrist-watch band "electrodes" were placed ½ inch apart on a wrist and provided 25K+/−1K ohms with little variation in view of small movements as compared to large jumps with smaller electrodes when moved over a small skin scab or other stratum corneum variance or movement from site to site.

Sensor drivers were also tested. The drive circuit to the body's electrodes could be a constant current source or a simple voltage drive through a known resistance. If a constant current drive is used, it was contemplated that its high side compliance voltage could be made large enough to "punch through" skin top layer, dead cells, oils, etc. so no skin preparation or large settling time would be required. A 20-volt compliant, 50 micro-amp source was tried on various wrist locations using a quarter sized electrode. It was found that after one to three seconds of application that a tingle was felt and then the measured body voltage drop would suddenly reduce down to a "long-term" normal value. This provides a way to improve GSR measurement stability and reduce time to first measurement. Lower voltages were also used. It was found that a 25 uA source provided a good compromise between electrode "plating" and having enough current to measure GSR adequately. An 8-volt compliant constant current source was deemed sufficient.

Constant resistance drivers were used and have the advantage that high GSR values never cause a signal input overload. However, the voltage to GSR mapping is non-linear. Either type of driver was adequate, the choice of which to sue depending on the range of GSR expected and computer linearization capability.

After using the above sources, Vgsr began to change upward. It was found that the electrodes were being plated with body salts and discoloring. Thus, for long term monitoring, AC drive or polarity reversing methods are beneficial. A new circuit was designed and built which reversed the constant current drive upon command and would, further, amplify the change in Vgsr around a preset value since it is so much smaller with wrist placement of the electrodes. Studies with the device revealed that simple low frequency AC drivers would likely give poor results due to electrolytic voltage settling with each polarity reversal. Thus, the GSR system should: a) reverse polarity of drive with each measurement, b) wait for electrolytic effects to die down before making a GSR measurement, and c) discontinue current drive until another measurement is needed.

Thus, a preferred system of the present invention has the following characteristics: a) permits wait period for GSR drive to equilibrate before a measurement is made, b) permits wait period of two to five minutes for the electrode interface to stabilize after first "wearing" the device, c) to address motion artifact, ability to take a series of readings and take a medium value, d) use lower drive voltages (e.g., under 9vdc), e) flip polarity of drive with GSR measurement series, and f) use adaptive sampling methods (e.g., take readings until stability is seen). In one preferred configuration, the electrode is a wrist watch with the expansion stainless steel band being one electrode and the watch's underbelly being the other.

All publications and patents mentioned in the above specification are herein incorporated by reference. Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A system for remote monitoring of a human child, comprising:
   1) a device comprising a processor configured to:
      a) receive a transmitted signal from a remote device on said child, said transmitted signal conveying a fear response of said child and audio or video information about said child's ambient environment;
      b) convert said transmitted signal into a format that permits display of data corresponding to said transmitted signal on a display device;
      c) organize said data to display a fear indication on said display device; and
      d) provide secured access to said display of said fear indication to a user registered to access information related to said child;
   2) a fear monitoring device that measures galvanic skin resistance adapted to be used on said child; and
   3) a mobile phone device configured to collect audio or video information about said child's ambient environment, wherein said fear monitoring device transmits a signal upon detecting a threshold fear response of said child to said mobile phone and wherein said mobile phone transmits said signal and said audio or video information to said device comprising said processor.

2. The system of claim 1, wherein said processor is located in a computer.

3. The system of claim 1, wherein said processor is located in a hand-held device.

4. The system of claim 3, wherein said hand-held device is a phone.

5. The system of claim 3, wherein said hand-held device is a personal digital assistant.

6. The system of claim 1, wherein said format that permits display of said data comprises a data format transmissible and displayable over an Internet.

7. The system of claim 1, wherein location of said subject is further displayed.

8. The system of claim 1, wherein said processor is configured to detect said fear response of said subject at two or more time points and to determine whether a change in said fear response has occurred at one or more of the time intervals between said two or more time points.

9. The system of claim 1, wherein said processor is configured to notify said user when said fear response of said subject deviates from a predetermined range.

10. The system of claim 1, wherein said processor is configured by software.

11. The system of claim 1, wherein said transmitted signal is a satellite signal.

12. The system of claim 1, wherein said transmitted signal is a telephone signal.

13. The system of claim 1, wherein said processor stores user information selected from the group consisting of user codename, social security number, and telephone number.

14. The system of claim 1, wherein a body position of said subject is displayed.

15. The system of claim 1, wherein an appearance of said subject is displayed.

16. The system of claim 1, wherein said remote fear monitoring device comprises a wrist band.

17. The system of claim 1, wherein said remote fear monitoring device comprises a galvanic skin resistance drive and a set of electrodes.

18. The system of claim 17, wherein said fear monitoring device is configured to allow the galvanic skin resistance drive to equilibrate before a measurement is taken to detect a fear response.

19. The system of claim 17, wherein said fear monitoring device is configured to take a series of readings and calculate a medium value, prior to transmitting a signal.

20. The system of claim 17, wherein said fear monitoring device is configured to reverse polarity of said galvanic skin resistance drive with each measurement taken.

* * * * *